US00PP30519P3

(12) United States Plant Patent
Stemkens

(10) Patent No.: US PP30,519 P3
(45) Date of Patent: May 21, 2019

(54) ***IBERIS* PLANT NAMED 'IBSZ0006'**

(50) Latin Name: *Iberis sempervirens*
Varietal Denomination: IBSZ0006

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,787

(22) Filed: Apr. 24, 2018

(65) Prior Publication Data

US 2019/0045695 P1 Feb. 7, 2019

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
See application file for complete search history.

(56) References Cited

PUBLICATIONS

PLUTO Plant Variety Database Feb. 2, 2019.*

* cited by examiner

*Primary Examiner* — Annette H Para
(74) *Attorney, Agent, or Firm* — Dale Skalla

(57) ABSTRACT

A new *Iberis* plant named 'IBSZ0006' particularly distinguished by its very large pure white flowers that are early flowering, grass green foliage and a compact, mounded plant habit.

1 Drawing Sheet

Latin name of the genus and species of the plant claimed: *Iberis sempervirens*.

Varietal denomination: 'IBSZ0006'.

BACKGROUND OF THE NEW PLANT

The present invention comprises a new *Iberis*, botanically known as *Iberis sempervirens*, and hereinafter referred to by the variety name 'IBSZ0006'.

'IBSZ0006' is a product of a planned breeding program. The new cultivar 'IBSZ0006' has very large pure white flowers that are early flowering, grass green foliage and a compact, mounded plant habit.

'IBSZ0006' originates from an open pollination in a greenhouse in April 2010 in Enkhuizen, The Netherlands. The female parent was an unpatented, proprietary plant designated 'P1252-3' with medium size white flowers, darker green foliage and is less branched when compared to 'IBSZ0006'.

The male parent of 'IBSZ0006' is unknown. It was a cloud of pollen of all plants available. The resultant seed was sown in August 2010 in Enkhuizen, The Netherlands.

'IBSZ0006' was selected as one flowering plant within the progeny of the stated cross in March 2011 in a greenhouse in Enkhuizen, The Netherlands.

The first act of asexual reproduction of 'IBSZ0006' was accomplished when vegetative cuttings were propagated from the initial selection in June 2011 in a greenhouse in Enkhuizen, The Netherlands.

BRIEF SUMMARY OF INVENTION

Horticultural examination of plants grown from cuttings of the plant initiated in June 2011 in Enkhuizen, The Netherlands, and continuing thereafter, has demonstrated that the combination of characteristics as herein disclosed for 'IBSZ0006' are firmly fixed and are retained through successive generations of asexual reproduction.

'IBSZ0006' has not been observed under all possible environmental conditions. The phenotype may vary significantly with variations in environment such as temperature, light intensity and day length.

A Plant Breeder's Right for this cultivar has not been applied for in the European Union on Aug. 1, 2017, No. 2017/1902. 'IBSZ0006' has been made publicly available prior to the effective filing date of this application, notwithstanding any disclosure that may have been made less than one year prior to the effective filing date of this application by the inventor or another who obtained 'IBSZ0006' directly from the inventor.

The following traits have been repeatedly observed and are determined to be basic characteristics of the new variety. The combination of these characteristics distinguishes this *Iberis* as a new and distinct variety.

BRIEF DESCRIPTION OF THE PHOTOGRAPHS

The accompanying photographic drawing shows typical flower and foliage characteristics of 'IBSZ0006' with colors being as true as possible with an illustration of this type.

The photographic drawing shows in FIG. 1 a flowering plant of the new variety.

DETAILED BOTANICAL DESCRIPTION

The plant descriptions and measurements were taken in Enkhuizen, The Netherlands under natural light in March 2017. These plants were approximately 34 weeks old and were grown in 13 cm pots in hoop-house trials. The plants used for the photographs were about 34 weeks old growing in Enkhuizen, The Netherlands and the photographs were taken in March 2017.

Color Chart used: Royal Horticultural Society Colour Chart (R.H.S.) 2001

TABLE 1

DIFFERENCES BETWEEN THE NEW VARIETY 'IBSZ0006' AND A SIMILAR VARIETY

| | 'IBSZ0006' | 'Snow Cone' (Not patented) |
|---|---|---|
| Flower size: | Larger | Smaller |
| Plant size: | Larger | Smaller |
| Branching habit: | More branching | Less branching |

Plant:
- *Form, growth and habit.*—Dense, compact, mounded and branched.
- *Plant height.*—12 cm.
- *Plant height (inflorescence included).*—14 cm (without pot).
- *Plant width.*—25.0 cm.

Roots:
- *Number of days to initiate roots.*—About 8 days at about 18 degrees C.
- *Number of days to produce a rooted cutting.*—3.5 weeks at 18 degrees C.
- *Type.*—Fine, fibrous, white, moderate branched.
- *Color.*—RHS N155B but whiter.

Foliage:
- *Arrangement and attachment.*—Alternate simple-decussate, sessile.
- *Immature, leaf color, upper surface.*—RHS 138A.
- *Lower surface.*—RHS 138B.
- *Mature, leaf color, upper surface.*—RHS 137A.
- *Lower surface.*—RHS 137A.
- *Length.*—3-4 cm.
- *Width.*—0.4-0.6 cm.
- *Shape.*—Linear to slightly oblanceolate.
- *Base shape.*—Attenuate, clasped to stem.
- *Apex shape.*—Rounded.
- *Margin.*—Entire.
- *Texture, upper surface.*—Glabrous.
- *Lower surface.*—Glabrous.
- *Color of veins, upper surface.*—RHS 137B.
- *Color of veins, lower surface.*—RHS 143B.
- *Venation pattern.*—Only main middle vein visible.
- *No petiole.*—Sessile.

Stem:
- *Quantity of main branches.*—About 5-8, with each many lateral branches.
- *Color of stem.*—RHS 146C and upper side turning purple: RHS N185A.
- *Length of stem.*—10-12 cm (including peduncle).
- *Diameter.*—0.4 cm.
- *Length of internodes.*—1-1.3 cm.
- *Texture.*—Rough, no hairs.

Inflorescence:
- *Type.*—Short simple corymb.
- *Quantity of inflorescences per plant.*—More than 80.
- *Inflorescence length.*—2-4 cm.
- *Inflorescence width.*—3.5-4.5 cm at widest point.
- *Lastingness of individual blooms on the plant.*—About 14 days.
- *Fragrance.*—None.

Bud (just before opening/showing color):
- *Color.*—RHS 150D.
- *Length.*—0.4 cm.
- *Width.*—0.4 cm.
- *Shape.*—Globose.
- *Pedicel color.*—RHS 143B.
- *Pedicel length.*—0.6 cm.
- *Pedicel diameter.*—0.5 cm.
- *Pedicel texture.*—Smooth.

Corolla:
- *Shape of corolla.*—4 petals — 2 small and 2 large, smaller and bigger petals are opposite of each other.
- *Petal, length.*—0.8-1.6 cm.
- *Petal, width.*—0.6-0.9 cm.
- *Floret depth.*—1.2 cm.
- *Flower depth.*—3.5-4 cm.
- *Petal (all) color, upper surface.*—RHS N155B.
- *Lower surface.*—RHS N155B.
- *Upper/shorter petals.*—
- *Length.*—0.7 cm.
- *Width.*—0.5 cm.
- *Shape.*—Obovate.
- *Apex shape.*—Rounded.
- *Margin.*—Entire.
- *Lower/longer petals.*—
- *Length.*—1.4 cm.
- *Width.*—0.8 cm.
- *Shape.*—Obovate to truncate.
- *Apex shape.*—Rounded.
- *Margin.*—Entire.
- *Petal (all) texture, upper surface.*—Papillose.
- *Lower surface.*—Papillose.

Calyx:
- *Quantity.*—4 sepals.
- *Color, upper surface.*—RHS 144B.
- *Lower surface.*—RHS 144A.
- *Length.*—0.25 cm.
- *Width.*—0.25 cm.
- *Shape.*—Ovate.
- *Apex shape.*—Rounded.
- *Base.*—Fused.
- *Margins.*—Entire.
- *Texture, upper/inner surface.*—Smooth.
- *Lower/outer surface.*—Smooth.

Reproductive organs:
- *Gynoecium.*—
- *Pistil quantity.*—1.
- *Length.*—0.4-0.6 cm.
- *Style color.*—RHS 144B.
- *Style length.*—0.25-0.3 cm.
- *Stigma color.*—RHS 151C.
- *Stigma shape.*—Lobed.
- *Ovary.*—Not very discernable.
- *Androecium.*—
- *Stamens, quantity.*—6.
- *Color of filaments.*—RHS 145D-RHS 184A.
- *Length of filaments.*—0.2-0.3 cm.
- *Anther color.*—RHS 154C.
- *Anther length.*—0.05 cm.
- *Anther shape.*—Oval.
- *Pollen amount.*—No pollen has been observed.

*Fertility/seedset.*—Neither seed nor fruit production has been observed.

*Disease/pest resistance.*—Resistance to pathogens and pests common to *Iberis* has not been observed.

*Drought tolerance and cold tolerance.*—Hardy perennial. Tolerates high temperature to at least 30 degrees C. Tolerates low temperatures to degrees minus 25 C. No specific drought tolerance has not been observed.

What is claimed is:

1. A new and distinct variety of *Iberis* plant named 'IBSZ0006' substantially as illustrated and described herein.

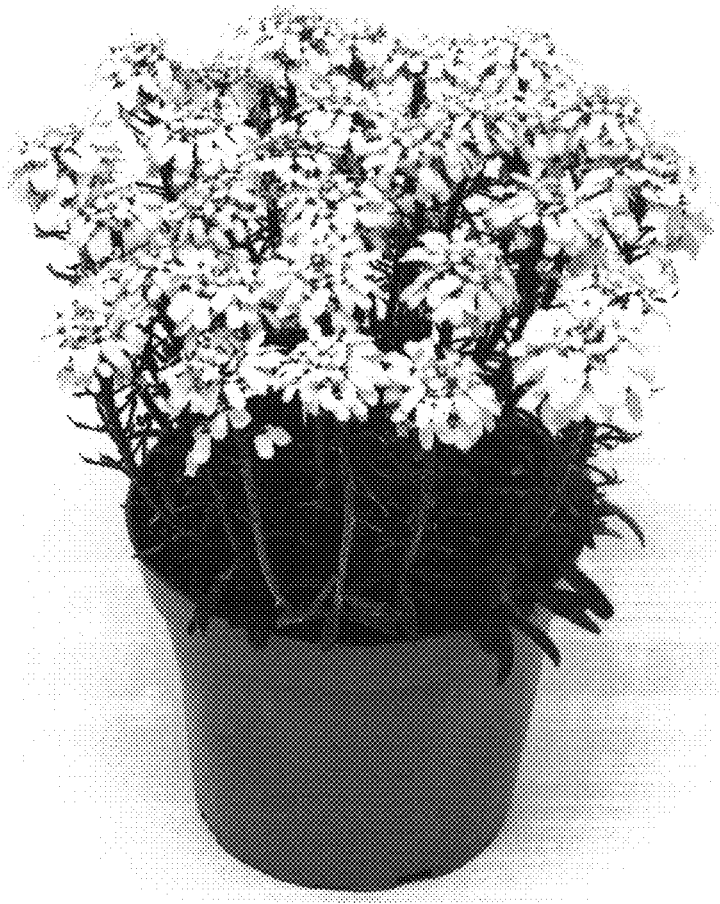

* * * * *